US008474305B2

(12) United States Patent
Brown et al.

(10) Patent No.: US 8,474,305 B2
(45) Date of Patent: Jul. 2, 2013

(54) SYSTEMS AND METHODS TO DETECT PARTICULATE DEBRIS IN A FLUID

(75) Inventors: Nathan K. Brown, Palmyra, VA (US); Fritz J. Friedersdorf, Earlysville, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 563 days.

(21) Appl. No.: 12/695,095

(22) Filed: Jan. 27, 2010

(65) Prior Publication Data

US 2010/0192679 A1  Aug. 5, 2010

Related U.S. Application Data

(60) Provisional application No. 61/148,414, filed on Jan. 30, 2009.

(51) Int. Cl.
  *G01N 15/08*  (2006.01)
(52) U.S. Cl.
  USPC ........................................................ 73/61.73
(58) Field of Classification Search
  USPC ............................................. 73/61.71, 61.73
  See application file for complete search history.

(56) References Cited

U.S. PATENT DOCUMENTS

| 5,702,592 | A | 12/1997 | Suri et al. | |
|---|---|---|---|---|
| 5,968,371 | A * | 10/1999 | Verdegan et al. | 210/739 |
| 6,334,959 | B1 | 1/2002 | Sutton et al. | |
| 6,855,249 | B2 | 2/2005 | Moskaritolo | |
| 6,993,414 | B2 | 1/2006 | Shah | |
| 7,182,858 | B2 | 2/2007 | Brown et al. | |
| 8,135,547 | B2 * | 3/2012 | Phattaranawik et al. | 702/35 |

OTHER PUBLICATIONS

Dempsey, P., et al, Investigation of Tapered Roller Bearing Damage Detection Using Oil Debris Analysis, IEEE Aerospace Conference Proceedings, 2006.
Dempsey, P., et al., NASA/TM-2006-214380, Tapered Roller Bearing Damage Detection Using Decision Fusion Analysis, 2006.
Idelchik, I.E., Handbook of Hydraulic Resistance—3$^{rd}$ Ed., CRC Press 1994, pp. 522-523.
Bair, S., The Variation of Viscosity with Temperature and Pressure for Various Real Lubricants, J. Tribo., Apr. 2001, vol. 123, Issue 2, 433 (Abstract Only).

(Continued)

*Primary Examiner* — Hezron E Williams
*Assistant Examiner* — Paul West
(74) *Attorney, Agent, or Firm* — Nixon & Vanderhye P.C.

(57) ABSTRACT

Methods and systems are provided for detecting presence of a target particulate of predetermined size (e.g., engine wear debris) in a fluid (e.g., an engine lubricant) by providing at least one pair of serially fluid-connected upstream test and downstream reference filtration elements in the fluid. At least the upstream test filtration element has a filtration size rating that is sufficient to remove a predetermined amount of the target particulate from the fluid. The differential pressure of the fluid may then be measured (e.g., by suitable pressure transducers) across each of the test and reference filtration elements. By comparing the differential pressure across the test filtration element to the differential pressure across reference filtration element, the presence of the target particulate in the fluid can thereby be detected by an increase in differential pressure across the test filtration element in comparison to the differential pressure across the reference filtration element. The methods and systems of the invention thus allow for the detection of target particulates that is independent of the fluid flow rate and/or temperature (viscosity, density).

23 Claims, 3 Drawing Sheets

OTHER PUBLICATIONS

Armour, J., and Cannon, J., "Fluid Flow Through Woven Screens", AIChE Journal, May 1968, vol. 14, No. 3, pp. 415-419.

Madhaven, Monitoring Fluid System Debris via Diagnostic Filters, DTIC AD-A325 558 Apr. 22-26, 1996.

Visyx Fluid Property Sensor Business Overview, Measurement Specialties, Jan. 2008.

Day, The Secret's, Filter debris analysis and differential pressure monitoring can reveal pending disaster—and help prevent it, Tribology & Lubrication Technology, Feb. 2008.

Rosenberg, Lubricant Condition Monitoring Using Filter Debris Analysis, Reprinted from Int'l Condition Monitoring Conference, Pensacola, FL, Apr. 18-22, 2004.

* cited by examiner

FIG. 3

SYSTEMS AND METHODS TO DETECT PARTICULATE DEBRIS IN A FLUID

CROSS-REFERENCE

This application is based on and claims domestic priority benefits under 35 USC §119(e) from U.S. Provisional Application Ser. No. 61/148,414 filed on Jan. 30, 2009, the entire content of which is expressly incorporated hereinto by reference.

FIELD

The disclosed embodiments herein relate to systems and methods for monitoring debris in a fluid. Especially preferred embodiments are adapted to monitor debris in a fluid (e.g., oil, transmission fluid, hydraulic fluid and the like) associated with a vehicle's propulsion system (e.g., a jet propulsion system) so as to aid in the assessment of engine diagnostics and/or maintenance.

BACKGROUND

Most lubricant circulation systems contain some form of filtration to remove debris from the lubricant to extend component life. As the filter ages and becomes more loaded with particulate, it becomes more restrictive thereby requiring greater line pressure to cause the lubricant to flow through the filter at the same flow rate. The differential pressure ($\Delta P$) across the filter is therefore a reasonable indicator of the filter's loading level and remaining useful life. Filter differential pressure monitoring is widely utilized on aircraft and large trucks to assess when a filter is fully loaded and requires replacement.

Monitoring the level of debris in a lubricant circulation system can provide an indication of abnormal component wear requiring maintenance action. In this regard, component wear in a propulsion system (e.g., wear associated with bearings, gears, shafts and the like) is typically evidenced by particulate metal that has been removed from the component through wear and deposited in a circulating lubricant (e.g., oil). Thus, by analyzing the type and amount of metal particles in a propulsion system's circulating lubricant, an operator can assess the relative health of the propulsion system components to facilitate maintenance decisions.

Several prior methods for detecting wear processes and failure progression of propulsion systems that include bearings and gears require intrusive instrumentation, large high frequency data sets, and sophisticated analysis methods. For example, vibration monitoring is a prominent method for continuously assessing the relative health of propulsion system components. However, vibration monitoring requires vibration sensors to be distributed throughout the system with the need for access of the various vibration sensor components and the ability to isolate and interpret the vibration responses. These requirements hinder or preclude the use of vibration techniques in many applications. Also significant damage to the propulsion system may occur before such damage is detected through vibration monitoring thereby giving operators little time to react to impending failure.

Recently U.S. Pat. No. 7,299,683 to Nikkels et al (the entire content of which is expressly incorporated hereinto by reference) has disclosed a metal particle sensor to detect presence of metal particles in the lubricant flow. However, since the metal particle sensor is sensitive to lubricant flow rate, it must be corrected for the effects of the local flow rate in order to provide an accurate particulate measurement. In order to correct for such flow rate sensitivity, the system of Nikkels et al '683 suggest using a differential pressure measurement across an orifice to measure flow rate in proximity to the metal particle sensor. The combined use of a metal particle sensor and a differential pressure across an orifice thereby serves to correlate the output of the metal particle sensor to the flow rate as determined by the differential pressure across the orifice.

Other techniques for detecting wear debris in lubricant systems include magnetic chip collectors. However, such magnetic chip collectors require operators to periodically remove the collected chips to allow for physical inspection and determination of the type and amount of wear debris that has been collected. While magnetic chip collectors overcome the complexity of implementing a vibration sensor system, they do not provide the operator with real time data that can be used to warn of impending component failure. Also chip detectors only collect particles that come into proximity of the magnetic collection element which are known to have poor collection efficiencies.

Systems which employ a single differential pressure measurement have been used to monitoring the amount of debris collected by a filter element (colloquially known as "filter loading") so as to maintain the filter element in good condition. Such systems however are incapable of assessing the type and/or size of the debris removed from the fluid by the filter element, especially in the small quantities associated with impending component failure. As such, such single differential pressure measurement systems cannot determine if the collected debris is abnormal and/or potentially associated with failure progression of a component. In addition, such conventional single differential pressure measurement systems are also not sufficiently sensitive to detect the early stages of wear damage to components associated with a propulsion system, such as bearings, gears or other engine wear parts.

Moreover, while the use of single differential pressure measurements is known for detecting filter loading, such a technique is dependent on both fluid temperature and flow rate. The required measurement system resolution for use in detecting minute amounts of wear debris could therefore only be achieved through extremely accurate flow rate and temperature measurements at the filter element(s).

It would especially be desirable if self-compensating detection systems and/or methods could be provided that were capable of detecting debris in a circulating fluid that is independent of flow rate and/or temperature (viscosity, density) of the fluid so that the wear processes and failure progression of components could be determined in real time. It is towards providing such systems and methods that the present invention is directed.

SUMMARY OF EXEMPLARY EMBODIMENT

Certain preferred forms of the present invention are embodied in systems and methods whereby self-compensating detection of debris in a circulating fluid is detected independent of the fluid flow rate and/or temperature (viscosity, density). More specifically, serially fluid-connected fluid filtration elements are provided that allow a target particulate, e.g., engine wear debris, to be captured by an upstream one of the filtration elements (termed a test filtration element) so that the differential pressure across the element can be compared to the differential pressure across a downstream one of the filtration elements (termed a reference filtration element). By employing a flow rate and temperature independent algorithm, the onset of abnormal component wear can be ascertained in real time that will assist the operator to develop suitable maintenance strategies prior to the onset of engine performance degradation and/or damage. One principal benefit of the embodiments of the invention described herein is its robustness to uncontrolled changes in fluid properties, such as flow rate, density and viscosity that would otherwise obscure the differential pressure response over a single filtration element that may have captured small levels of damage-related particulates.

According to certain embodiments of the invention, methods and systems are provided for detecting presence of a target particulate of predetermined size (e.g., wear debris associated with engine component wear such as critical engine bearings and/or gears) in a fluid (e.g., an engine lubricant) by providing at least one pair of serially fluid-connected upstream test and downstream reference filtration elements in the fluid. At least the upstream filtration element will have a filtration size rating so as to be capable of removing a predetermined amount of the target particulate from the fluid. The differential pressure of the fluid may then be measured (e.g., by suitable pressure transducers) across each of the test and reference filtration elements. By comparing the differential pressure across the test filtration element to the differential pressure across reference filtration element, the presence of the target particulate in the fluid can thereby be detected by an increase in differential pressure across the test filtration element in comparison to the differential pressure across the reference filtration element. Moreover, such detection is independent of fluid properties such as flow rate, density and/or viscosity.

Some embodiments may further include a primary filtration element in series downstream of at least one pair of serially fluid-connected test and reference filtration elements, wherein the primary filtration element has a filtration size rating that is smaller that the filtration size rating of the at least the test filtration element.

The presence of the target particulate may be detected according to other embodiments by causing the pressure transducers to generate an output signal which is indicative of the differential pressures across the test and reference filtration elements, respectively. Suitable data processing circuitry may thus receive such differential pressure signals and thereby calculate a ratio of the differential pressure across the test filtration element to the differential pressure across the reference filtration element to determine presence of the particulate debris in the fluid.

Certain other embodiments will issue a signal in response to detecting the debris being present in the fluid in an amount above a predetermined set point, e.g., so as to alert maintenance personnel and/or the on-board operator.

Especially preferred embodiments provide for methods and systems for detecting particulate wear debris of engine components in a closed loop engine lubricant circulation system. According to these embodiments, an upstream test filtration element and a downstream reference filtration element are installed in series in the closed loop engine lubricant circulation system so that engine lubricant flows serially through the test filtration element and then through the reference filtration element. The filtration size rating of at least the upstream test filtration element is selected so that its filtration media captures a predetermined amount (preferably substantially all) of the wear debris in the fluid while allowing substantially all of the normal debris associated with the engine lubrication (e.g., engine dust, soot and/or seal wear typically associated with engine operation) to pass therethrough. In such a manner therefore the test filtration element will become substantially more loaded with the wear debris as compared to the downstream reference filtration element.

The differential pressure of the lubricant across each of the test and reference filtration elements may thus be measured, for example, by pressure transducers. Data processing circuitry may be provided so as to compare the differential pressure across the test filtration element to the differential pressure across reference filtration element to thereby detect presence of the particulate wear debris in the fluid by an increase in differential pressure across the test filtration element in comparison to the differential pressure across the reference filtration element.

These and other aspects of the present invention will become more clear after careful consideration is given to the following detailed description of a presently preferred exemplary embodiment thereof.

BRIEF DESCRIPTION OF ACCOMPANYING DRAWINGS

The disclosed embodiments of the present invention will be better and more completely understood by referring to the following detailed description of exemplary non-limiting illustrative embodiments in conjunction with the drawings of which.

DETAILED DESCRIPTION

A. Technical Focus

The embodiments disclosed herein address the need to detect small amounts of lubrication system debris within a given particulate size range. One practical example of this need is detecting bearing wear particulate in an engine lubrication system to permit safe shutdown of the engine prior to failure. In many situations, the amount of wear debris generated during an impending failure event is small compared to the total capacity of the primary filter. In this case, the filter's differential pressure sensitivity to the damage event is low and may not register a useful response even with high resolution pressure monitoring hardware.

In order to increase the sensitivity to anomalous debris, preferred embodiments of the present invention will include serially fluid-connected filtration elements upstream of the primary filter can be utilized so as to capture only the debris of interest (that is, metal particulates associated with component wear) while allowing normal system debris (e.g., typical engine particulates, such as sludge) to pass into the main filter. Monitoring differential pressures across the filtration elements thereby provides much more sensitive detection of particles in the size of interest since the surface areas of the filtration elements are significantly less than the surface area associated with the primary filter element.

Differential pressure across a screen is a function of the debris loading level, but is also strongly dependent on fluid properties such as flow rate and viscosity. Nominal changes in flow rate and fluid temperature can produce the same level of differential pressure change as typical levels of wear debris. Using the conventional single screen approach, therefore, one must have explicit knowledge of the fluid flow rate and viscosity (temperature) in order for the effects of such variables to be canceled using an empirical formulation. For systems where such flow and viscosity information is readily available, debris monitoring can be accomplished using the conventional technique of a single screen having a single differential pressure transducer.

In many cases, however, flow rate and temperature (viscosity) information is not readily available and thus requires additional instrumentation. Under these circumstances, the embodiments disclosed herein provide a self-compensating approach by comparing the differential pressures across two similar filtration elements without the need to provide additional flow and temperature instrumentation inputs.

B. Definitions

As used herein and in the accompanying claims, the following terms have the meanings as set forth below:

The term "wear debris" means solid particulate matter in a fluid, typically and engine lubricant fluid, having an average particle diameter of about 100 microns or larger, usually about 150 microns and larger, and typically about 200 microns and larger. Wear debris is typically associated with the in service degradation of critical engine bearing and/or gear components and may exhibit a substantially planar, irregular disc-shaped particulate morphology with an average thickness of about 5 microns and larger, typically about 10 microns and larger. Wear debris associated with some engines, e.g., aircraft turbine engines, may have a substantially planar, irregular disc-shaped particulate morphology exhibiting an average particle diameter of between about 200 to about 300 microns or larger and an average thickness of between about 10 microns to about 25 microns or larger.

The term "normal debris" is meant to refer to granular, generally irregular prismatic-shaped solid particulates that are typically present in an engine lubricant after a period of normal engine operation, including for example engine dust, soot and/or seal wear. Normal debris will typically have an average particle diameter of about 120 microns and smaller. Usually normal debris in engines will correspond generally to ISO Standard 12103-1 (1992) (incorporated hereinto fully by reference) for A4 Coarse particulate wherein about 90 vol. % of the particulate has an average particle diameter of about 80 microns or smaller.

The term "particle diameter" is the smallest diameter of a sphere which entirely contains a particle.

The term "filtration size rating" is the size in microns corresponding to the smallest average particle diameter which is substantially entirely (i.e., 99 wt. % or more) captured by the filtration media.

The term "filtration media" refers to any structure capable of physically separating solid particulates from a fluid based on the particulate size. The filtration media may thus be in the form of woven and/or nonwoven filaments, porous solid materials (e.g., porous ceramic filter elements) and the like.

C. Detailed Description of Exemplified Embodiment

Figure 1:
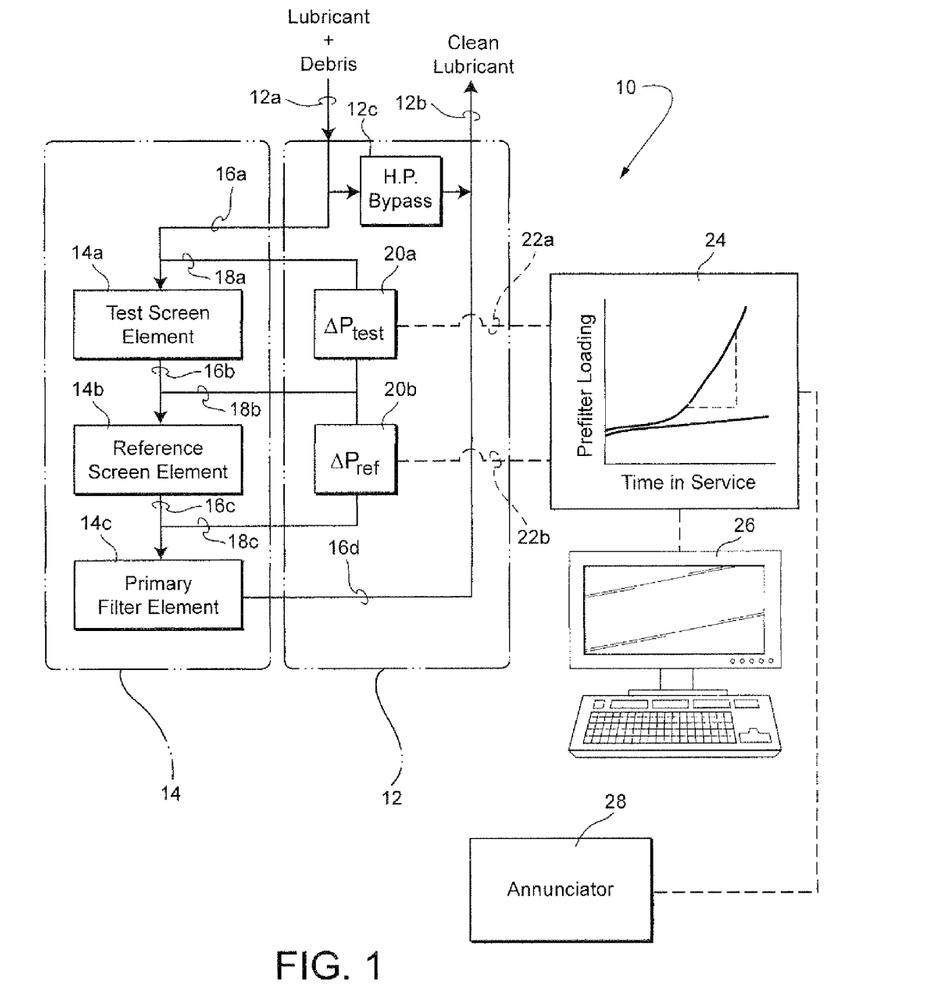
FIG. 1 is a schematic diagram of a system according to an embodiment of the present invention for detecting component wear debris in a circulating lubrication fluid associated with a propulsion system.

Accompanying FIG. 1 schematically depicts one presently preferred system 10 that embodies the present invention. In this regard, the system 10 as depicted in FIG. 1 is shown as a lubrication system associated with an engine (e.g., an aircraft engine). However, the system 10 which embodies the present invention may likewise be employed in other fluid systems, e.g., hydraulic systems, transmission systems, and the like, in which detection of a target particulte is desired.

The system 10 depicted in FIG. 1 generally includes self-contained filter housing unit 12 fluid connected to a filter cartridge unit 14. The filter housing and filter cartridge units 12, 14, respectively, are mounted on-board the vehicle at a suitable location in the engine's lubricant circulation system and thus receives the "dirty" engine lubricant (i.e., lubricant plus debris (including component wear debris and normal debris)) via line 12a and returns "clean" engine lubricant (i.e., lubricant that has been substantially stripped of all debris by filtration within the filter cartridge unit 14) to the system via line 12b. The filter housing 12 most preferably includes a high pressure bypass valve 12c to allow the lubricant from the inlet line 12a to be bypassed directly to the outlet line 12b, for example, in the event of increased backpressure due to filter blockage to thereby permit the continual supply of lubricant to the engine.

The filter cartridge 14 is most preferably provided with a test filtration element 14a, a reference filtration element 14b and a primary filter element 14c fluid connected to one another in series via lubricant lines 16a, 16b and 16c. The various fluid lines connecting the filter housing unit 12 to the filter cartridge unit 14 may be provided as fixed connections or may if desired be provided with suitable structural elements to allow the filter cartridge 14 to be removably coupled to the filter housing unit 12. Removability of the filter cartridge 14 relative to the filter housing unit 12 would thus be desirable so that a filter cartridge 14 having fresh elements 14a, 14b and 14c may quickly and efficiently replace a filter cartridge 14 that has come to the end of its useful service life. Thus, by way of example only, the filter cartridge 14 may be threadably coupled with the filter housing unit 12 so that once seated, the fluid communication of the various lubricant lines (e.g., lines 16a, 18a, 18b, 18c and 16d) is established.

Wear debris associated with engine bearing and/or gear failure exhibits specific sizes that allow for it to be captured by the test filtration element 14a while the normal debris (non-wear debris) in the lubricant will pass therethrough. In especially preferred embodiments, the test filtration element 14a is selected for the operational environment so that that it exhibits a filtration size rating which captures at least 50 wt. %, preferably at least about 80 wt. %, and advantageously at least about 90 wt. %, of wear debris having an average particle diameter of about 100 microns or larger, preferably about 150 microns or larger, and most preferably about 200 microns and larger. In especially certain preferred embodiments, the filtration size rating of the test filtration element 14a is such that at least 50 wt. %, preferably at least about 80 wt. %, and advantageously at least about 90 wt. % of wear debris having an average particle diameter of between about 200 to about 300 microns, and larger and an average thickness of between about 10 microns to about 25 microns, and larger is captured thereby.

The reference filtration element 14b on the other hand will have a filtration size rating that is at least comparable to or greater than the filtration size rating of the test filtration element 14a. That is, the reference filtration element 14b is selected so that it has a filtration size rating such that virtually all (i.e., substantially 100 wt. %) of the wear debris that is not captured by the upstream test filtration element 14a is allowed to pass through the reference filtration element 14b. This ensures that any non-captured (unfiltered) wear debris passing through the test filtration element 14a will likewise pass through the downstream reference filtration element 14b along with substantially 100% of the normal debris in the lubricant. Thus, if the test filtration element 14a captures at least about 50 wt. % of the wear debris, then the reference filtration element 14b will have a filtration size rating such that substantially all of the remainder of the wear debris passing through the test filtration element 14a will likewise pass through the reference filtration element 14b. Similarly, substantially all of the normal debris will thus pass through both the test filtration element 14a and the reference filtration element 14b. In such a manner, the reference filtration element 14b will not become loaded with either that portion of the wear debris (if any) or the normal debris which is allowed to pass through the upstream test filtration element 14a by virtue of its filtration size rating. In some embodiments, the filtration size rating of the reference filtration element 14b may be equal to the filtration size rating of the test filtration element 14a.

By comparison with the primary filter element 14c, the test and reference filtration elements 14a, 14b, respectively, have a much larger filtration size rating as compared to the downstream primary filter element 14a. As such, the relatively coarse wear debris in the lubricant will be captured by the test filtration element 14a while the more fine particulates associated with normal (non-wear) debris will pass through both the test and reference filtration elements 14a, 14b, respectively, and be captured by the relatively finer downstream primary filter element 14c.

The actual filtration size ratings of the test and reference filtration elements 14a, 14b may thus be selected based on a number of operating parameters well within the skill of those in this art. By way of example only, one may engineer a specific filtration system embodying the present invention so as to sacrifice sensitivity of the filtration media to the wear debris in order to decrease sensitivity of the filtration media to normal debris and vice versa. Thus, a lesser amount of wear debris can be captured by the test filtration element 14a in order to ensure that substantially all normal debris passes through both the test and reference filtration elements 14a, 14b, respectively. Suffice it to say that ideally one would strive to capture substantially all (i.e., substantially 100 wt. %) of the wear debris by the test filtration element 14a so that virtually no wear debris passes on to the reference filtration element 14b and then on to the primary filtration element 14c. Conversely of course it would be ideal if substantially all (i.e., substantially 100 wt. %) of the normal debris passes through both the test and reference filtration elements 14a, 14b, respectively, and is captured by the primary filtration element 14c. However, less than these ideal parameters may in fact be the engineered standard in practice for embodiments of the present invention. Such embodiments will nonetheless be sufficient to provide advance warning, for example, of potential adverse critical engine component wear so as to prompt a maintenance event before potential catastrophic engine damage is encountered.

The test and reference screens 14a, 14b can be of any type of filtration media that may be conventionally employed for the filtration of particulates from fluids. Thus, woven and non-woven filtration media may be employed formed from polymeric or non-polymeric (e.g., metal, ceramic, cellulosic and the like) fibers. Alternatively or additionally, the filtration media employed in the screens 14a, 14b may a sintered porous ceramic or like material that is inert to the fluids being filtered. Similarly, the filter element 14c may include filtration media that is formed of materials that are the same or different from those employed for the screens 14a, 14b, although the average pore size of such filtration media is substantially smaller than the average pore size of the screens 14a, 14b for the reasons discussed previously.

The "dirty" lubricant entering the filter housing 12 via line 12a is thus initially directed to the upstream side of the test filtration element 14a via line 16a. Any wear debris in the lubricant will thus be removed by the test filtration element 14a so that the lubricant can then be directed sequentially through the reference filtration element 14b via line 16b and through the downstream primary filter element 14c via line 16c in that order. The filtration size ratings of the test and reference filtration elements 14a, 14b, respectively, are sufficiently large so as to allow the more fine non-wear debris in the lubricant to pass therethrough into line 16c. Such non-wear debris will thus be captured by the primary filter element 14c so that the "clean" lubricant can pass to the filter housing 12 via line 16d and then on to outlet line 12b where it can be returned to the engine lubricant system.

The filter housing 12 also contains pressure transducers 20a, 20b which are connected operatively to the upstream and downstream sides of the test and reference filtration elements 14a and 14b via pressure sensing lines 18a, 18b and 18c. The pressure transducers 20a, 20b therefore sense the differential pressure $\Delta P\text{test}$, $\Delta P\text{ref}$ across the test and reference filtration elements 14a, 14b, respectively, and output respective signals indicative of the differential pressure $\Delta P\text{test}$, $\Delta P\text{ref}$ via signal lines 22a, 22b to data processing circuitry (DPC) 24. As the wear debris removed from the lubricant by the test filtration element 14a increases, the differential pressure $\Delta P\text{test}$ sensed by the pressure transducer 20a will likewise increase. On the other hand, the differential pressure $\Delta P\text{ref}$ sensed by the pressure transducer 20b will remain substantially constant. As will be discussed in greater detail below, algorithms in the DPC 24 can thus compare the differential pressure data $\Delta P\text{test}$ and $\Delta P\text{ref}$ so as that the wear progression can be monitored, e.g., via an input/output or interface device 26 (e.g., a remote or on-board unit). In the event the wear data indicates excessive wear has occurred (i.e., the amount of detected wear debris exceeding some predetermined set point), an alert signal can be generated and issued to a remote or on-board audible and/or visual annunciator 28 so as to alert maintenance personnel and/or the on-board operator of the vehicle of potential excessive engine component wear. Remedial action can thus be taken quickly in response to such annunciation to avoid engine damage.

The system 10 as described above can be configured as a wireless and/or a wired wear debris monitor that is either hardwired to supply power or can be battery powered. Thus, for example, the system 10 may be provided as an on-board monitoring system which can transmit data wirelessly (e.g., via suitable data link) to a remote monitoring site. The debris monitor system 10 can also be used in conjunction with other sensing elements for improved knowledge about the power system conditions, ambient conditions, and the like.

Empirical relationships for predicting pressure drop across woven screens are known. In this regard, Equation 1 presented below is a generalized form of the relationship that has been developed previously. Equation 1 provides an insight into the functional dependence of the differential pressure with respect to fluid properties: density ($\rho$), kinematic viscosity ($v$), and velocity ($u$). Note that in this case we assume that density and viscosity have explicitly known functionalities with respect to local fluid temperature (T).

$$\Delta P(u,T) = A(Bu\rho(T)v(T) + u^2\rho(T)) \quad \text{(Equation 1)}$$

It can be observed from Equation 1 the differential pressure across a given screen is highly dependent on fluid velocity, density, and viscosity. Of these parameters, fluid density and viscosity are particularly difficult to measure in-situ. Typically, prior filter health monitoring approaches attempt to accommodate the viscosity dependence by directly measuring temperature and then estimating viscosity using predetermined viscosity-temperature curves. For high resolution wear debris sensing, such a prior approach can be unreliable due to variability in the fluid viscosity as it ages. The system 10 as described above therefore accommodates the uncertainty in flow rate, density, and viscosity as described below.

Constants A and B in Equation 1 are dependent on screen geometric parameters, such as thickness, pore diameter, and percent open area which are constant for a given screen and debris load level. These constant values will change for different screen loads as the effective open area and effective screen thickness are both affected by the presence of trapped debris. Constant A in Equation 1 has been shown experimentally to be much more sensitive to screen loading than Constant B which is favorable for the dual-screen approach embodied by the present invention.

The system 10 as described above will preferably have the test and reference filtration elements 14a, 14b within close proximity to one another (e.g., within about six inches, preferably within about three inches, or less) to ensure that the fluid velocity and temperature are substantially the same at both screen locations. If it is assumed that the Constant B parameter is identical for both the test and reference filtration elements 14a, 14b, respectively, the general pressure drop relationship given in Equation 1 may be rearranged to relate the measured differential pressures. Thus assuming that the Constant B parameter is identical for both the test and reference screens, and further assuming that the fluid properties are identical at both screens, Equation 1 can be applied to both screens and simplified to:

$$\frac{\Delta P_{test}}{\Delta P_{ref}} = \frac{A_{test}}{A_{ref}} \qquad \text{(Equation 2)}$$

where ΔPtest and ΔPref are the differential pressures across the test and reference filtration elements 14a, 14b and Atest and Aref are non-dimensional constants for both filtration elements 14a, 14b, respectively. In particular, Atest will change with increased wear debris loading while Aref will remain constant as its load does not change appreciably over time. The clear implication of Equation 2 is that an accurate measure of the loading state (Atest) for the test filtration element 14a is not predicated on knowledge of fluid velocity, viscosity and density.

Figure 2:
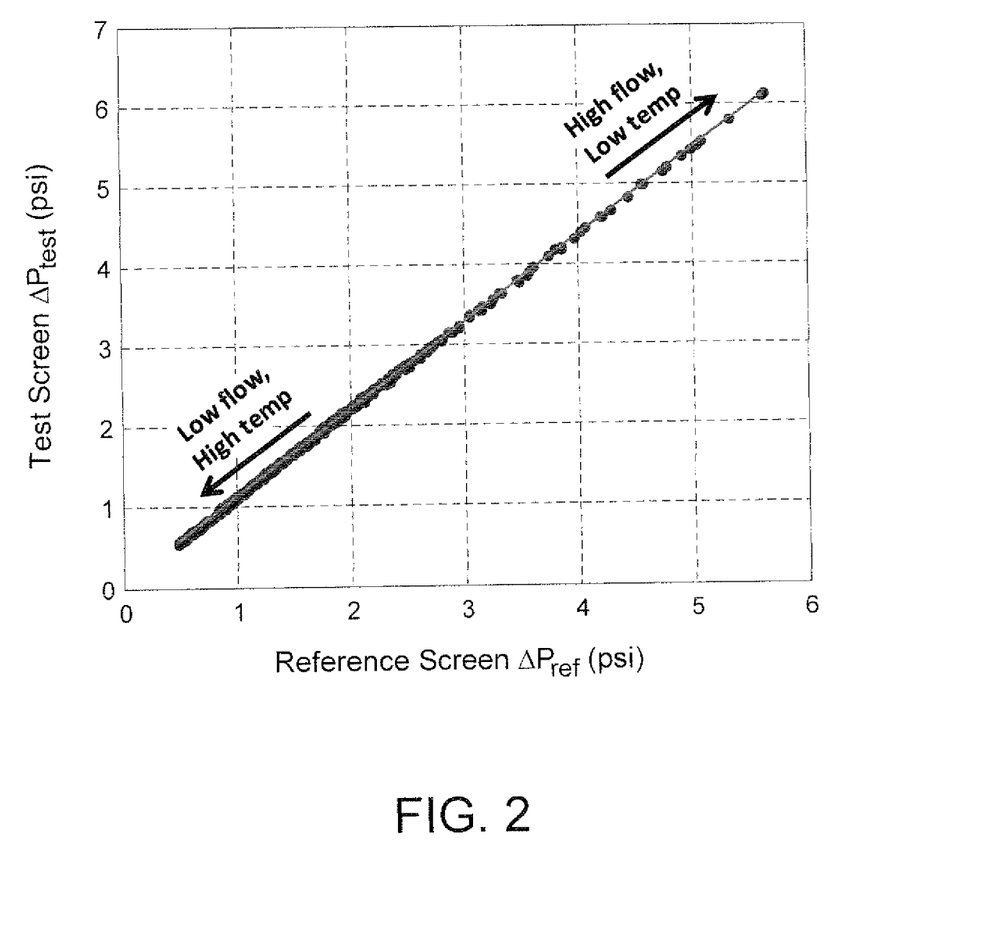
FIG. 2 is a graph showing the differential pressure ($\Delta P$) response of the test filter element with respect to the $\Delta P$ response of the reference filter element over a wide range of flow rates in accordance with an embodiment of the invention.

For a given screen loading state (Constant A), Equation 2 dictates that there will be a linear relationship between the two differential pressures, regardless of fluid density, viscosity and flow rate. Accompanying FIG. 2 shows this relationship by plotting the ΔPtest response of the test filtration element 14a with respect to the ΔPref response of the reference filtration element 14b over a wide range of flow rates and temperatures. The slope of the line in the plot of FIG. 2 is effectively the ratio of Atest/Aref of Equation 2 above. Therefore, as Atest increases with higher wear debris loads, the slope of the line plot of FIG. 2 will also increase.

The linear relationship between the two screen differential pressures permits straightforward calculation of the unknown restriction parameter, Atest, of the test filtration element 14a by simply acquiring ΔPref and ΔPtest data pairs without regard to the specific values of the flow parameters that affect the individual screen differential pressures.

D. Examples

An experiment was conducted to demonstrate the ability of a dual-screen differential pressure monitoring system as shown in FIG. 1 to reliably resolve small additions of lubrication system debris without requiring additional compensation for flow velocity or thermal viscosity effects. For this experiment, the two screens consisting of stainless steel tri-layer sintered mesh with a filtration size rating of 140 microns were employed as the test and reference filtration elements 14a, 14b, respectively. The two screens were collocated as close as possible in the flow loop test stand, approximately three inches apart in a section of 0.93 inch inner diameter seamless stainless steel tubing. Normal flange taps were drilled into the tubing on either side of both filtration elements for sampling the static pressure. Differential pressure was measured across each screen using very high accuracy Kulite XTL-3-375 differential pressure transducers. The test fluid was fresh Mobil Jet II synthetic aircraft engine lubricant, qualified to MIL-PRF-23699. Flow rates ranged between approximately 2.7 and 6.7 gallons per minute, and fluid temperature was controlled between 68-78° C.

Figure 3:
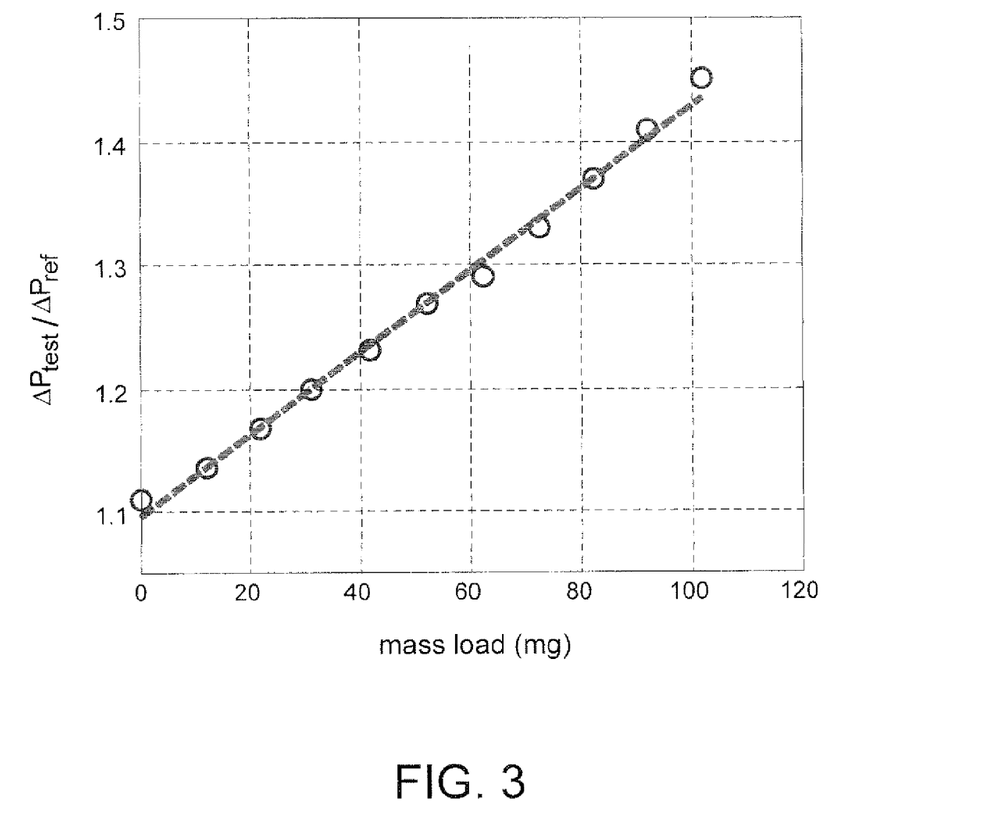
FIG. 3 is a graph showing the linearity of response between total captured mass (mg) of the wear debris versus the ratio of the $\Delta P$ of the test filter element to the $\Delta P$ of the reference filter element in accordance with an embodiment of the present invention.

Eleven debris loading levels were studied, consisting of a clean screen run followed by ten additions of nominally 10 mg batches of 150-500 micron size steel test contaminate. At each load level, the differential pressures for both screens were obtained concurrently. The differential pressure ratio across the test and reference screens ($\Delta P_{test}/\Delta P_{ref}$) was calculated for each loading state. Accompanying FIG. 3 illustrates the results, showing a clear linear trend between total captured debris mass and the screen pressure ratio. A primary conclusion from this experiment is that the two-screen measurement system in accordance with the present invention easily resolved small changes in particulate loading, without explicit flow and viscosity correction, despite the highly changing flow rates and dynamic temperature profile.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A method for detecting presence of target particulates of predetermined size in a fluid comprising both target particulates of the predetermined size and smaller sized non-target particulates, the method comprising:
   (a) providing at least one pair of serially fluid-connected upstream test and downstream reference filtration elements in a fluid, wherein the upstream test filtration element has a filtration size rating sufficient to remove a predetermined amount of the target particulates of the predetermined size from the fluid and to allow substantially all of the smaller sized non-target particulates to pass therethrough, and wherein the downstream reference filtration element has a filtration size rating sufficient to allow both any remaining portion of the target particulates of the predetermined size not removed by the test filtration element and substantially all of the smaller sized non-target particulates to pass therethrough;
   (b) providing a primary filtration element in series downstream of the at least one pair of serially fluid-connected filtration elements, wherein the primary filtration element has a filtration size rating that is smaller than the filtration size rating of the test filtration element so as to capture substantially all of any remaining portion of the target particulates and the smaller sized non-target particulates passing through the downstream reference filtration element;
   (c) measuring differential pressure of the fluid across each of the test and reference filtration elements; and (d) comparing the differential pressure across the test filtration element to the differential pressure across the reference filtration element to thereby detect presence of the target particulates in the fluid by an increase in differential pressure across the test filtration element in comparison to the differential pressure across the reference filtration element.

2. A method as in claim 1, wherein step (c) is practiced by using pressure transducers to measure upstream and downstream pressure conditions across each of the filtration elements.

3. A method as in claim 2, wherein step (d) comprises (d1) generating an output signal from the pressure transducers indicative of the differential pressures across the test and reference filtration elements, respectively, and (d2) calculating a ratio of the differential pressure across the test filtration element to the differential pressure across the reference filtration element to determine presence of the target particulates in the fluid.

4. A method as in claim 1, which comprises providing a signal in response to detecting an amount of the target particulates being present in the fluid above a predetermined set point.

5. A method of detecting particulate wear debris of engine components in a lubricant comprising both particulate wear debris of predetermined size and normal particulate debris having a size smaller than the wear debris in a closed loop engine lubricant circulation system, the method comprising:
(a) installing an upstream test filtration element and a downstream reference filtration element in series upstream of a primary filtration element in the closed loop engine lubricant circulation system so that engine lubricant flows serially through the test filtration element, the reference filtration element and then through the primary filtration element, wherein the upstream test filtration element has a filtration size rating sufficient to remove a predetermined amount of the particulate wear debris from the lubricant and to allow substantially all of the smaller sized normal particulate debris to pass therethrough, and wherein the downstream reference filtration element has a filtration size rating sufficient to allow both any remaining portion of the particulate wear debris of the predetermined size not removed by the test filtration element and substantially all of the smaller sized normal particulate debris to pass therethrough, and wherein the primary filtration element has a size rating that is smaller than the filtration size rating of at least the test filtration element so as to capture substantially all of any remaining portion of the particulate wear debris and the smaller sized normal particulate debris passing through the downstream reference filtration element;
(b) measuring differential pressure of the lubricant across each of the test and reference filtration elements; and
(c) comparing the differential pressure across the test filtration element to the differential pressure across reference filtration element to thereby detect presence of the particulate wear debris in the fluid by an increase in differential pressure across the test filtration element in comparison to the differential pressure across the reference filtration element.

6. A method as in claim 5, wherein step (b) is practiced by using pressure transducers to measure upstream and downstream pressure conditions across each of the test and reference filtration elements.

7. A method as in claim 6, wherein step (c) comprises (c1) generating an output signal from the pressure transducers indicative of the differential pressures across the test and reference filtration elements, respectively, and (c2) calculating a ratio of the differential pressure across the test filtration element to the differential pressure across the reference filtration element to determine presence of the particulate wear debris in the fluid.

8. A method as in claim 5, which further comprises providing a signal in response to detecting the wear debris being present in the fluid in an amount above a predetermined set point.

9. A system for detecting presence of target particulates of predetermined size in a fluid comprising both target particulates of the predetermined size and smaller sized non-target particulates, the system comprising:
a test filtration element having a filtration size rating which is capable of removing a predetermined amount of the target particulates from the fluid yet allow substantially all of the smaller sized non-target particulates to pass therethrough;
a reference filtration element serially fluid-connected downstream of the test filtration element and having a filtration size rating that is at least comparable to or greater than the filtration size rating of the test filtration element to allow both any remaining portion of the target particulates of the predetermined size not removed by the test filtration element and substantially all of the smaller sized non-target particulates to pass therethrough;
a primary filtration element fluid-connected in series downstream of the test and reference filtration elements, wherein the primary filtration element has a filtration size rating that is smaller than the filtration size rating of at least the test filtration element so as to capture substantially all of any remaining portion of the target particulates and the smaller sized non-target particulates passing through the downstream reference filtration element;
pressure transducers for measuring differential pressure of the fluid across each of the test and reference filtration elements and issuing differential pressure signals indicative of the differential pressure across the test and reference filtration elements, respectively; and
data processing circuitry for receiving and comparing the differential pressure signals generated by the pressure transducers to thereby detect presence of the target particulates in the fluid by an increase in differential pressure across the test filtration element in comparison to the differential pressure across the reference filtration element.

10. A system as in claim 9, wherein the data processing circuitry calculates a ratio of the differential pressure across the test filtration element to the differential pressure across the reference filtration element to determine presence of the target particulates in the fluid.

11. A system as in claim 9, wherein the data processing circuitry generates a signal in response to detecting the target particulates being present in the fluid in an amount above a predetermined set point.

12. A system for detecting particulate wear debris of engine components in a lubricant comprising both particulate wear debris of predetermined size and normal particulate debris having a size smaller than the wear debris in a closed loop engine lubricant circulation system, the system comprising:
an upstream test filtration element and a downstream reference filtration element serially fluid-connected in the closed loop engine lubricant circulation system so that engine lubricant is capable of flowing serially through the test filtration element and then through the reference filtration element, wherein the test filtration element has a filtration size rating that is sufficient to remove a predetermined amount of the particulate wear debris from the lubricant and to allow substantially all of the smaller sized normal particulate debris to pass therethrough, and wherein the downstream reference filtration element has a filtration size rating sufficient to allow both any remaining portion of the particulate wear debris of the predetermined size not removed by the test filtration element and substantially all of the smaller sized normal particulate debris to pass therethrough;

a primary filtration element fluid-connected in series downstream of the test and reference filtration elements, wherein the primary filtration element has a filtration size rating that is smaller than the filtration size rating of at least the test filtration element so as to capture substantially all of any remaining portion of the wear debris and the smaller sized normal particulate debris passing through the downstream reference filtration element;

first and second pressure transducers operatively connected to the test and reference filtration elements for measuring differential pressure of the lubricant across each of the test and reference filtration elements and issuing first and second differential pressure signals indicative of the differential pressures measured across the test and reference filtration elements, respectively; and data processing circuitry for receiving and comparing the first and second differential pressure signals issued by the first and second pressure transducers to thereby detect presence of the particulate wear debris in the fluid by an increase in the differential pressure across the test filtration element in comparison to the differential pressure across the reference filtration element.

13. A system as in claim 12, wherein the data processing circuitry calculates a ratio of the differential pressure across the test filtration element to the differential pressure across the reference filtration element to determine presence of the particulate wear debris in the fluid.

14. A system as in claim 12, wherein the data processing circuitry generates a signal in response to detecting the particulate wear debris being present in the fluid in an amount above a predetermined set point.

15. A system as in claim 12, further comprising an annunciator for receiving the signal generated by the data processing circuitry.

16. A system as in claim 12, wherein the test and reference filtration elements are contained within a filter cartridge unit.

17. A system as in claim 16, wherein the first and second pressure transducers are contained within a filter housing unit which is fluid connected to the filter cartridge unit.

18. A system as in claim 17, wherein the filter housing unit includes an inlet and an outlet for the lubricant and adapted to being connected as part of the closed loop lubricant circulation system.

19. A system as in claim 18, wherein the filter housing includes a bypass valve for fluid connecting the lubricant inlet to the lubricant outlet of the filter housing to thereby bypass the filter cartridge unit.

20. A system as in claim 17, wherein the filter cartridge unit is removably connected to the filter housing unit.

21. A system as in claim 12, wherein the test filtration element has a filtration size rating to capture at least 50 wt. % of particulate wear debris having an average particle diameter of about 100 microns or larger.

22. A system as in claim 12, wherein the test filtration element has a filtration size rating to capture at least 90 wt. % of particulate wear debris having an average particle diameter of about 200 microns and larger.

23. A system as in claim 12, wherein the test filtration element has a filtration size rating to capture substantially 100 wt. % of the particulate wear debris so that substantially no particulate wear debris passes therethrough to the reference filtration element.

* * * * *